May 13, 1952 A. G. KALLE Plant Pat. 1,095
PEAR TREE
Filed Dec. 1, 1950
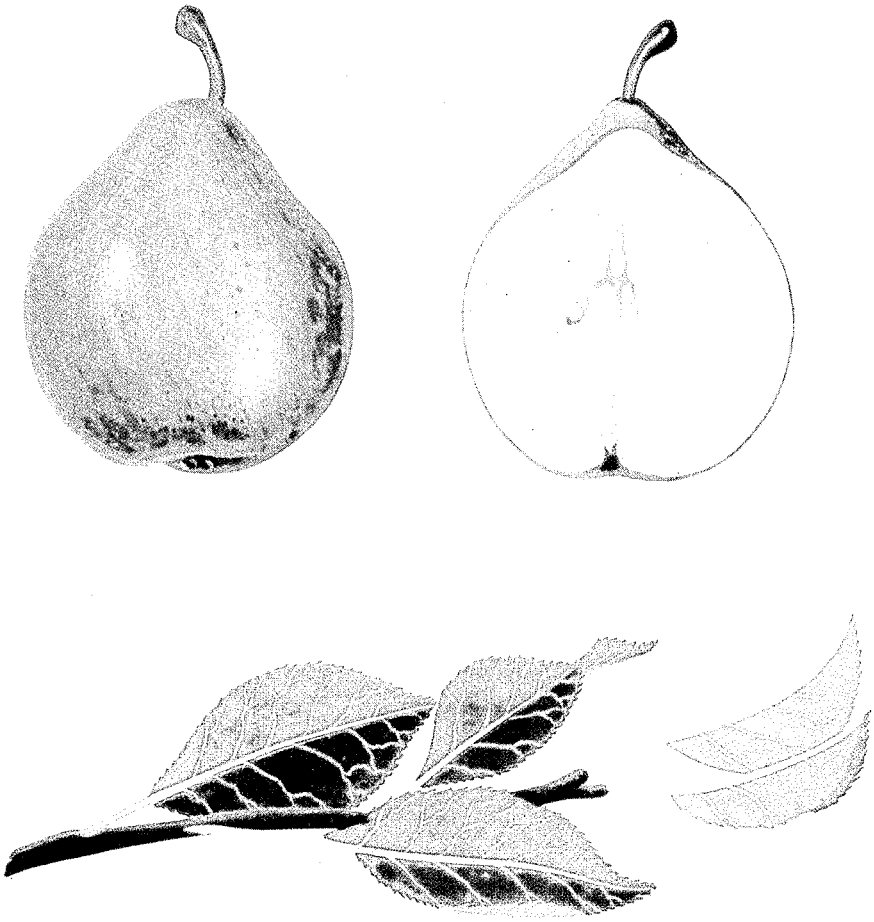
Inventor.
A. G. Kalle
By: Robert Cobb
Attorneys Patented May 13, 1952

Plant Pat. 1,095

UNITED STATES PATENT OFFICE 1,095

PEAR TREE

Adrian G. Kalle, South Haven, Mich., assignor to Stark Bro's Nurseries and Orchards Company, Louisiana, Mo., a corporation of Missouri Application December 1, 1950, Serial No. 198,510

1 Claim. (Cl. 47—62)

The present invention relates to a new and distinct variety of pear tree, originating as a bud sport of the variety known as "Clapp Favorite" (unpatented). The new variety was discovered by me in a cultivated orchard on my property in Van Buren County, Michigan.

This parent variety "Clapp Favorite" is principally characterized by its large, upright, spreading, round-topped form of the tree and its productivity of large, ovate, obtuse, pyriform, symmetrical fruit having a skin of pale lemon yellow color, mottled with bright red and dotted with numerous, small, russet dots. The flesh of the fruit is tinged with yellow, is tender and melting, juicy, sweet, rich and of very good quality.

The new variety is substantially identical in all respects with the aforementioned parent except that the skin of the fruit of the new variety is much more attractive and is substantially uniformly dark red in color all over, as hereinafter more particularly described.

Asexual reproduction of the new variety by grafting in Van Buren County, Michigan, shows that the foregoing characteristics come true to form and are established and transmitted through succeeding propagations.

The accompanying drawing shows specimens of the fruit and foliage of the new variety, the fruit being shown in both elevation and section.

The following is a detailed description of the new variety, based upon observations of specimens grown in Van Buren County, Michigan, with color terminology in accordance with Horticultural Color Guide and Ridgway's Color Standards and Nomenclature, as indicated, except where general color terms of ordinary dictionary significance are obvious:

Dates first and last picking: August 22nd–August 28th.

Tree: Large; vigorous; upright; tall; dense; rapid-growing; hardy; productive; regular bearing.

*Trunk.*—Medium stocky; shaggy.

*Branches.*—Medium thick; smooth. Color—Ochre Red, Plate XXVII, Color No. 5'' Tone *b* (Ridgway). Lenticels—medium large.

*Leaves.*—Length—3 inches; width—2⅛ inches. Medium small; medium wide; medium long; oval; taper-pointed; medium thin; smooth. Color—Scheeles Green, Color No. 860, page 175, vol. 2 (Horticultural Color Guide). Margin—finely serrate. Petiole—medium long; medium slender. Length—1¾ inches.

Flowers: Dates of first and full bloom—April 20th–April 25th. Blooms about midway between early and late varieties.

*Size.*—Large.

*Color.*—White.

Fruit: Maturity when described — hard ripe. Date—August 26th.

*Size.*—Uniform. Axial Diameter—3 inches. Transverse—2⅝ inches.

*Form.* — Obovate-obtuse-pyriform, tapering toward apex; symmetrical.

*Cavity.*—Unsymmetrical; very shallow; narrow; lipped, with fleshy ring around stem. Depth—$\frac{1}{16}$ inch. Breadth—⅜ inch. Markings—none.

*Basin.*—Symmetrical; wide flaring base; pubescent. Depth—⅛ inch. Breadth—¾ inch. Markings—none.

*Stem.*—Clubbed: stout; glabrous. Length—1¼ inches. Breadth—¼ inch. Color—Cinnamon Brown, Plate XV, Color 13', tone *k*, (Ridgway).

*Calyx.*—Open; segments persistent; narrowly acute; separated at base; ascending; reflexed from base at apex. Length—¼ inch. Outer surface and inner surface—pubescent.

*Eye.*—Large; open.

*Skin.* — Thick; tough; glossy; waxed. Dots—obscure; many; small; even; ruptured; circular. Color—Cinnamon Brown, Plate XV, Color 13', tone *k* (Ridgway). Distribution of dots—over all; most numerous toward base. Ground color—Purple Madder, Color No. 1028, page 181, vol. 2 (Horticultural Color Guide). Color markings—self-colored; dull. Bloom—wanting. Scarfskin—wanting. General color effect—deep purplish red.

Flesh: Juicy.

*Color of flesh*—Satiny; white with greenish tint.

*Texture.*—Firm; tender; grandular at core; melting.

*Flavor.* — Sweet; rich. Aroma — distinct. Quality—best.

Core: Distant.

*Bundle area.*—Medium small; broadly ovate; symmetrical; acute at base; in bundle opposite.

*Halves of area.*—Equal.

*Bundle.*—Color—Sea Foam Green, Plate XXXI, Color 27'', tone *f* (Ridgway). Inconspicuous in one whorl.

*Core lines.*—Meeting; in cross section indistinct.

*Carpellary area.*—Indistinct; small.

*Calyx tube.*—Pubescent; apex broadly obconic; shouldered. Depth of tube to shoulder—$\frac{1}{16}$ inch. Entire depth—¼ inch.

*Styles.*—Present; fleshy at base; united toward base; pubescent throughout.

*Stamens.*—In one whorl; marginal.

*Auxiliary cavity.*—Present.

*Seed cells.*—Axile; closed.

*Cell walls.*—Distant; thin; tough. Length—½ inch. Breadth—¼ inch. Longitudinal section—Broadly obovate; acute at apex. Surface — entirely smooth. Cross section—broad.

Seeds: Number perfect—5; imperfect—2. Number in one cell — 2. Length — $\frac{7}{16}$ inch. Breadth—$\frac{3}{16}$ inch.

*Form.*—Acuminate.

*Color.*—White with greenish tinge.

Use: Market; dessert.

Keeping quality: Medium. Number of days in ordinary storage—14.

I claim:

A new and distinct variety of pear tree, characterized as to novelty by its similarity to its parent variety "Clapp Favorite" (unpatented), but distinguished therefrom by the substantially uniform, attractive, all-over dark red color of the skin of its fruit, substantially as shown and described herein.

ADRIAN G. KALLE.

No references cited.